(12) United States Patent
Shtram et al.

(10) Patent No.: US 8,858,583 B2
(45) Date of Patent: Oct. 14, 2014

(54) LANCING DEVICE WITH INTEGRATED THERMOELECTRIC COOLER

(75) Inventors: Lior Shtram, Tel Aviv (IL); Marco De Angeli, Barzana (IT)

(73) Assignee: Flextronics AP, LLC, Broomfield, CO (US)

( * ) Notice: Subject to any disclaimer, the term of this patent is extended or adjusted under 35 U.S.C. 154(b) by 259 days.

(21) Appl. No.: 13/292,937

(22) Filed: Nov. 9, 2011

(65) Prior Publication Data

US 2013/0116719 A1  May 9, 2013

(51) Int. Cl.
  *A61B 17/32* (2006.01)
  *A61B 5/15* (2006.01)
  *A61B 5/151* (2006.01)

(52) U.S. Cl.
  CPC ..... *A61B 5/150022* (2013.01); *A61B 5/150503* (2013.01); *A61B 5/150412* (2013.01); *A61B 5/150129* (2013.01); *A61B 5/15117* (2013.01); *A61B 5/15113* (2013.01); *A61B 5/150954* (2013.01); *A61B 5/1519* (2013.01); *A61B 5/150786* (2013.01)
  USPC .......................................... 606/181; 600/583

(58) Field of Classification Search
  CPC ................... A61B 5/150129; A61B 5/150122; A61B 5/150412; A61B 5/150503
  USPC ..................... 606/181, 182; 604/22, 117, 110, 604/207–211; 600/583
  See application file for complete search history.

(56) References Cited

U.S. PATENT DOCUMENTS

| | | |
|---|---|---|
| 4,375,815 A | 3/1983 | Burns |
| 4,535,769 A | 8/1985 | Burns |
| 4,624,253 A | 11/1986 | Burns |
| 5,304,193 A | 4/1994 | Zhadanov |
| 5,356,420 A | 10/1994 | Czernecki et al. |
| 5,578,014 A | 11/1996 | Erez et al. |
| 5,976,165 A * | 11/1999 | Ball et al. ................ 606/180 |
| 6,045,567 A | 4/2000 | Taylor et al. |
| 6,210,420 B1 | 4/2001 | Mauze et al. |
| 6,352,514 B1 | 3/2002 | Douglas et al. |
| 7,288,102 B2 | 10/2007 | Griffin et al. |
| 7,357,808 B2 | 4/2008 | Kennedy |
| 7,438,694 B2 | 10/2008 | Boozer et al. |

(Continued)

FOREIGN PATENT DOCUMENTS

| | | |
|---|---|---|
| DE | 20001161 | 8/2000 |
| JP | 2004337296 A | 12/2004 |

(Continued)

*Primary Examiner* — Tuan V Nguyen
*Assistant Examiner* — Tin Nguyen
(74) *Attorney, Agent, or Firm* — Haverstock & Owens LLP (57) ABSTRACT

A lancing device (e.g., pen) having an integrated thermoelectric (e.g., Peltier) cooler. The lancing device includes an elongated heat accumulator having a lumen along which a piston having a lancet thereon translates back and forth. A Peltier device and a cooling ring are thermally interconnected to one end of the heat accumulator and include central apertures through which the lancet can extend. The lancing device also includes an integrated battery and microcontroller for supplying and regulating power to the Peltier device. Upon a current being sent through the Peltier device, a cold side of the Peltier device and hence the cooling ring gives up thermal energy and reduces in temperature. The cooling ring can then be placed about a body tissue (e.g., skin) for a period of time (e.g., 3-5 seconds) to desensitize the body tissue, and then the lancet can be fired to puncture the body tissue.

14 Claims, 5 Drawing Sheets

(56) References Cited

U.S. PATENT DOCUMENTS

| | | |
|---|---|---|
| 2003/0171715 A1 | 9/2003 | Hommann et al. |
| 2006/0217636 A1* | 9/2006 | Braig et al. .................. 600/583 |
| 2007/0255181 A1 | 11/2007 | Alvarez-Icaza et al. |
| 2008/0146966 A1* | 6/2008 | Levaughn et al. ............ 600/583 |
| 2010/0174237 A1* | 7/2010 | Halaka ......................... 604/114 |

FOREIGN PATENT DOCUMENTS

| | | |
|---|---|---|
| WO | 9321974 A1 | 11/1993 |
| WO | 2005096979 A1 | 10/2005 |
| WO | 2008081444 A2 | 7/2008 |
| WO | 2009146053 A1 | 12/2009 |
| WO | 2010109461 | 9/2010 |

* cited by examiner

LANCING DEVICE WITH INTEGRATED THERMOELECTRIC COOLER

BACKGROUND

Lancing devices (e.g., finger-pricking devices) are widely used in the medical field for applications such as skin-incisions and blood drawings. A typical lancing device has a lancet (e.g., blade, needle) and a mechanism or arrangement for its movement in two opposite longitudinal directions so as to puncture the skin of a patient and then to withdraw the lancet from the punctured skin. In some arrangements, the blade or needle is kept in a standby position until it is triggered by the user, who is typically a medical technician or personnel in charge of drawing the blood from a patient. In other arrangements, the user is required to manually set the assembly to an armed or cocked position before firing of the blade or needle can be triggered. Upon triggering, the blade or needle fires towards the skin of the patient (e.g., the finger) and makes an incision.

Insertion of a lancet into the skin of a patient is often, however, accompanied by a localized sensation of pain. In the case of people with diabetes who must test their blood glucose levels up to five or more times per day, this localized sensation of pain is only magnified. To date, efforts to minimize pain from lancing have largely focused on controlling the depth of penetration into the subject's skin at the lancing site. For example, many lancing devices include a depth-control mechanism for varying the depth of penetration, either by adjusting the distance of travel of the lancet tip, or by adjusting the position of an endcap through which the lancet protrudes during the lancing operation. While such advances in lancing device technology have, to some extent, reduced the pain associated with the lancing process, continued improvement in reducing pain and discomfort associated with the lancing process is needed.

SUMMARY

Disclosed herein is a lancing device including a housing with a housing wall having a first end, a second end defining a lancing opening, and a chamber extending between the first and second ends that includes a central axis. The housing wall includes a material that allows the housing wall to accumulate heat. The lancing device also includes a Peltier device for absorbing heat from a patient's skin and passing heat to the housing wall, the Peltier device having a hot side with a hot surface in thermal contact with the housing wall, a cold side with a cold surface interconnected to the hot side and that is adapted to receive heat from the patient's skin and pass the heat to the hot side, and a central aperture extending through the Peltier device between the hot and cold surfaces. The central aperture includes a central axis, and the central axes of the chamber and the central aperture are substantially collinear. The lancing device additionally includes a lancet that is translationally mounted within the chamber for movement between at least a cocked position and a lancing position and having a lancet tip for contact with the patient's skin in the lancing position. Also, a power source is mounted within the housing that is electrically interconnected to the Peltier device. The temperature of the cold side is adapted to decrease and the temperature of the hot side is adapted to increase when the power source passes a current through the Peltier device.

The housing wall may include a length extending between the first and second ends and the Peltier device may include a length extending between the hot and cold sides. Here, the length of the housing wall may be greater than the length of the Peltier device. The length of the housing wall may be between about 70-130 mm, or between about 90-110 mm.

The lancing device may include a cooling ring for cooling the patient's skin. The cooling ring may include a first surface in thermal contact with the cold surface, an opposed second surface for contact with the patient's skin, and a central aperture extending through the cooling ring between the first and second surfaces for receipt of the lancet tip in the lancing position. The central aperture of the cooling ring may have a central axis, and the central axis of the chamber, the central axis of the Peltier device and the central axis of the cooling ring may be substantially collinear. At least substantially an entirety of the cold surface may be in thermal contact with the first surface of the cooling ring. A diameter of the central aperture of the cooling ring may be less than a diameter of the central aperture of the Peltier device.

An outer diameter of the housing wall may be at least substantially equal to an outer diameter of the Peltier device. The power source may include a battery. The housing wall may include one or more metals (e.g., copper, aluminum, combinations thereof). The cooling ring may include aluminum.

Also disclosed herein is an apparatus including an elongated cylindrical heat accumulator having a first end, a second end defining an lancing opening, a chamber extending between the first and second ends, a length extending between the first and second ends, and a longitudinal axis extending along the chamber through a center of the heat accumulator. The apparatus also includes a Peltier device thermally connected to the second end of the heat accumulator and includes a hot side having a hot surface, a cold side having a cold surface, a length extending between the hot and cold surfaces, and a central aperture extending through the Peltier device between the hot and cold surfaces. A central axis of the central aperture of the Peltier device and the longitudinal axis of the chamber are substantially collinear. Additionally, the apparatus includes a cooling ring thermally connected to the Peltier device and opposed from the heat accumulator. The cooling ring includes a central aperture extending through the cooling ring, and a central axis of the central aperture of the cooling ring is collinear with the central axis of the central aperture of the Peltier device and the longitudinal axis of the chamber. The cooling ring includes a first surface in thermal contact with the cold surface and an opposed second surface for contact with the patient's skin, and at least substantially an entirety of the cold surface is in thermal contact with the first surface of the cooling ring. The apparatus also includes a lancet translationally mounted within the heat accumulator for movement between at least a cocked position and a lancing position. The lancet has a lancet tip for contact with the patient's skin when the lancet is in the lancing position.

A battery may be mounted within the heat accumulator that is electrically interconnected to the Peltier device. The Peltier device may be adapted to receive heat collected from a patient's skin from the cooling ring and pass the received heat to the heat accumulator to cool the patient's skin when the battery passes a current through the Peltier device as part of a lancing procedure on the patient's skin. A diameter of the central aperture of the cooling ring may be less than a diameter of the central aperture of the Peltier device.

DETAILED DESCRIPTION

While the disclosure is susceptible to various modifications and alternative forms, specific embodiments thereof have been shown by way of example in the drawings and are herein described in detail. It should be understood, however, that it is not intended to limit the disclosure to the particular form disclosed, but rather, the disclosure is to cover all modifications, equivalents, and alternatives falling within the scope and spirit of the disclosure as defined by the claims. For instance, while one type of triggering mechanism for a lancing device that allows a lancet to be pulled back and then "fired" into a patient's body tissue will be discussed and illustrated, it should be appreciated that numerous other types and arrangements of triggering mechanisms are also encompassed by the present disclosure.

Figure 1:
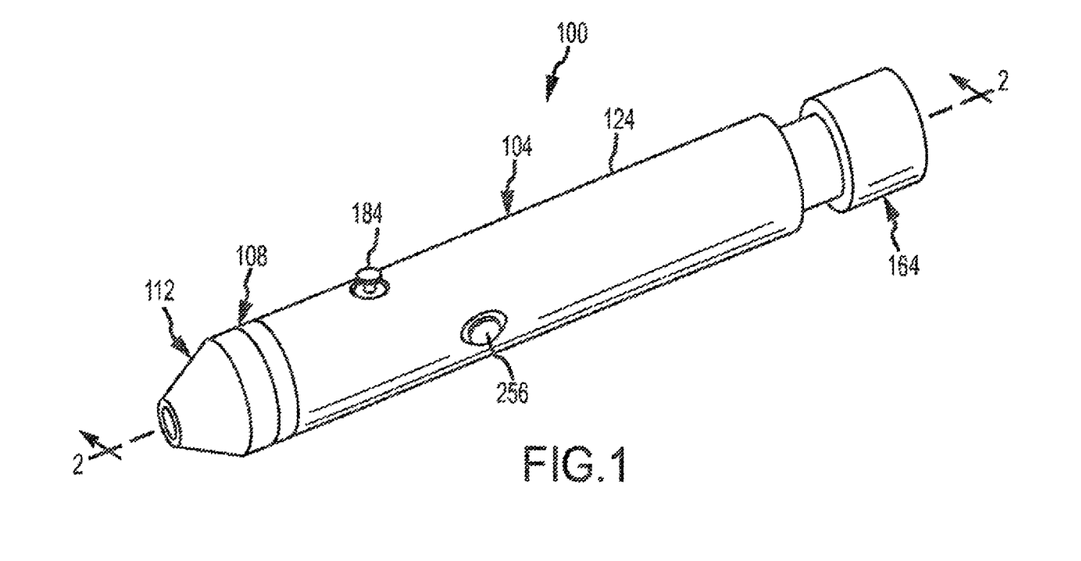
FIG. 1 is a perspective view of a lancing device according to one embodiment.
Figure 2:
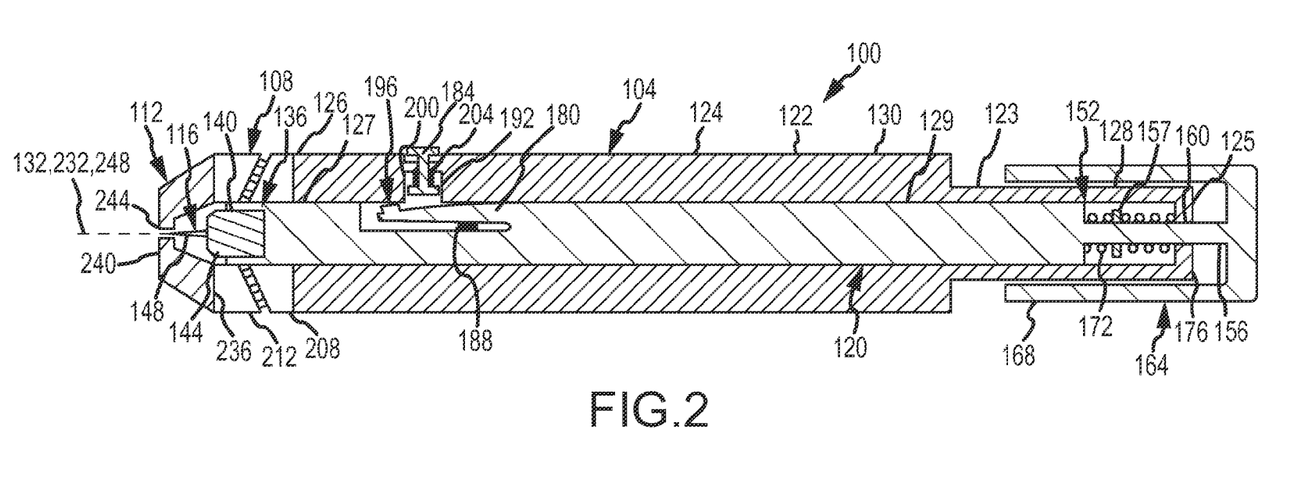
FIG. 2 is a cross sectional view of the lancing device along the lines 2-2 of FIG. 1 with a piston and lancet being in a relaxed position.

With initial reference to FIGS. 1-2, a lancing device 100 for sampling blood from a body tissue (e.g., skin) according to one embodiment is illustrated. FIG. 1 shows a perspective view of the lancing device 100 and FIG. 2 shows a cross-sectional view of the lancing device 100. The lancing device 100 may broadly include a housing 104, a Peltier device 108 (e.g., thermoelectric cooler), a cooling ring 112, a lancet 116 and a piston 120 that is translatable or slidable within the housing 104 to allow the lancet 116 to puncture a body tissue as part of a lancing procedure (e.g., skin pricking). As will be described more fully below, the Peltier device 108 serves to cool the particular portion of body tissue before the body tissue is punctured to reduce the localized sensation of pain typically encountered during a lancing procedure.

The housing 104 may include a housing wall 124 including body and tail portions 122, 123, a proximal or first end 125, a distal or second end 126 defining a lancing opening 127, and an internal chamber or lumen 128 along or through which the piston 120 may slide or translate along a longitudinal or central axis 132 of the housing 104 to move the lancet 116 between at least armed, relaxed and lancing positions. The housing wall 124 may include inside and outside surfaces 129, 130. As shown, the housing wall 124 may be in the form of an elongated cylindrical member although the housing wall 124 may have other than circular cross-sections (e.g., square, hexagonal). Additionally, the housing wall 124 may also be of such dimensions (e.g., length, thickness, i.e., the difference between an outside diameter and an inside diameter or distance between the inside and outside surfaces 129, 130) such that the housing wall 124 may function as a heat accumulator that receives and spreads out thermal energy received from the Peltier device 108 as will be described more fully below. In this regard, the housing wall 124 may be constructed of any appropriate material(s) that serve to receive and conduct thermal energy along the length of the housing wall 124 (e.g., metals). For instance, it has been found that copper and aluminum are suitable materials for this purpose. Additionally, any appropriate insulative shell or sheath (e.g., constructed of plastic) may be disposed about at least a portion of the housing wall 124, Peltier device 108 and/or cooling ring 112 to protect the various internal components of the lancing device 100, to isolate the thermal energy on the housing 104, to provide for a more comfortable grip for a user, and to provide a medium upon which designs, logos and the like can be deposited or otherwise formed, among other purposes.

The interface between the piston 120 and the inside surface 129 of the housing wall 124 may be designed such that there is little friction hindering the sliding motion of the piston 120 in the lumen 128. For instance, the piston 120 and the inside surface 129 may be made or coated with an appropriate low friction material (e.g., polytetrafluoroethylene). As another example, the interface between the piston 120 and the inside surface 129 may be lubricated and sealed against air leakage by any appropriate liquid lubricant. Other types of low friction materials and lubricants are also contemplated.

A distal or second end 136 of the piston 120 may include a cavity 140 in which a lancet block 144 of the lancet 116 may be appropriately secured (e.g., threaded connection, press-fit, welding). The lancet block 144 may include a lancet tip 148 at its distal end. Accordingly, when the piston 120 slides distally forward, the piston 120 pushes the lancet block 144, and therefore the lancet tip 148, forward to lance the body tissue. It is contemplated that the lancet block 144 and lancet tip 148 may be replaceable with a new, sterile lancet block 144 and lancet tip 148 after each lancing procedure.

In any event, a proximal or first end 152 of the piston 120 may include a shaft 156 appropriately attached thereto or formed thereon that extends backward through an aperture 160 in the tail portion 123 of the housing wall 124. The shaft 156 may include a flange 157, and may also be appropriately interconnected to a sleeve cap 164 which has a cylindrical sleeve 168 encircling the shaft 156 and the tail portion 123 of the housing wall 124. An actuating spring 172 may be positioned between the piston 120 and a back wall 176 of the tail portion 123 such that at least a portion of the actuating spring 172 is disposed on both sides of the flange 157. Thus, when the piston 120 is moved backward, the piston 120 and/or flange 157 compress the actuating spring 172 on the back wall 176 storing potential energy that may be used to fire the piston 120 and hence the lancet tip 148 into a patient's tissue.

Figure 3:
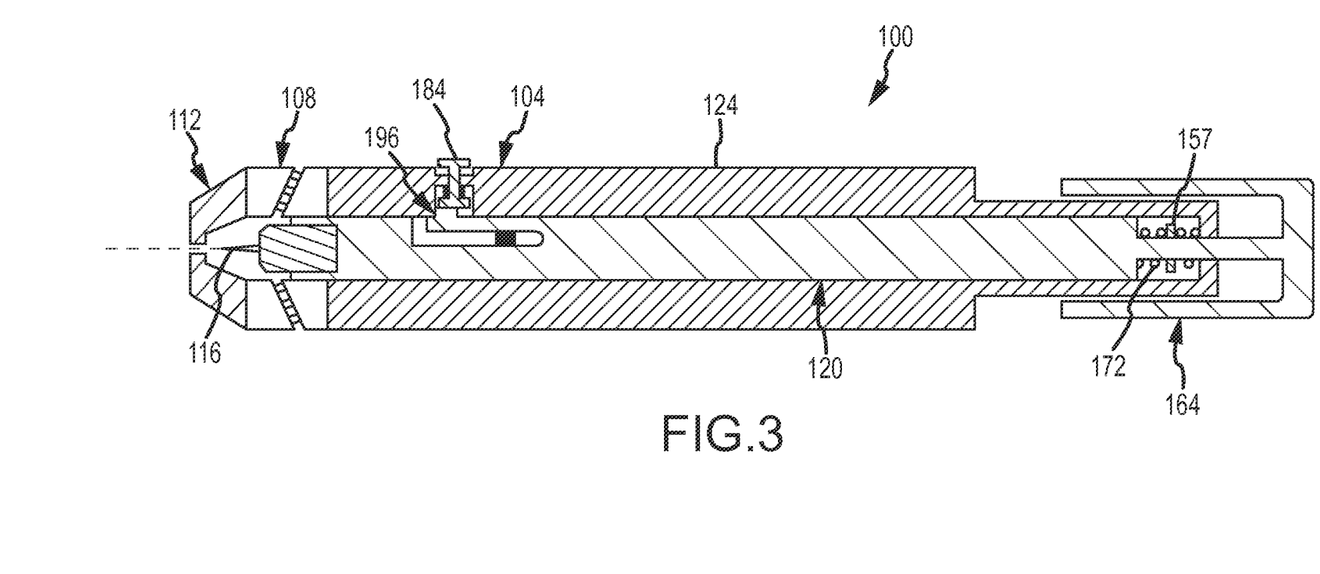
FIG. 3 is a cross sectional view similar to that in FIG. 2, but with the piston and lancet being in an armed position.

To prime the piston 120 and lancet 116 into a cocked or armed position, a cantilever 180 and triggering button 184 (e.g., push button, lever) are provided. The cantilever 180 may be appropriately attached to or formed as part of the piston 120 and may be urged away from the piston 120 towards the inside surface 129 of the housing wall 124 by a spring 188 situated between the cantilever 180 and the piston 120. Alternatively, the spring 188 may not be provided in the situation where the cantilever 180 includes enough resiliency such that it inherently tends to "spring" towards the inside surface 129. In any event, the inside surface 129 of the housing wall 124 may include a cavity 192 that is adapted to receive a protrusion 196 of the cantilever 180. In this regard, when the piston 120 is moved or pulled backwardly or rearwardly (e.g., via the sleeve cap 164) from the position illustrated in FIG. 2, the protrusion 196 of the cantilever 180 will eventually be pushed into the cavity 192 as illustrated in FIG. 3. When the backward pulling force is terminated, the compressed actuating spring 172 urges the piston 120 and/or flange 157 forward and the protrusion 196 catches on a wall 200 of the cavity 192 and is thereby retained.

Figure 4:
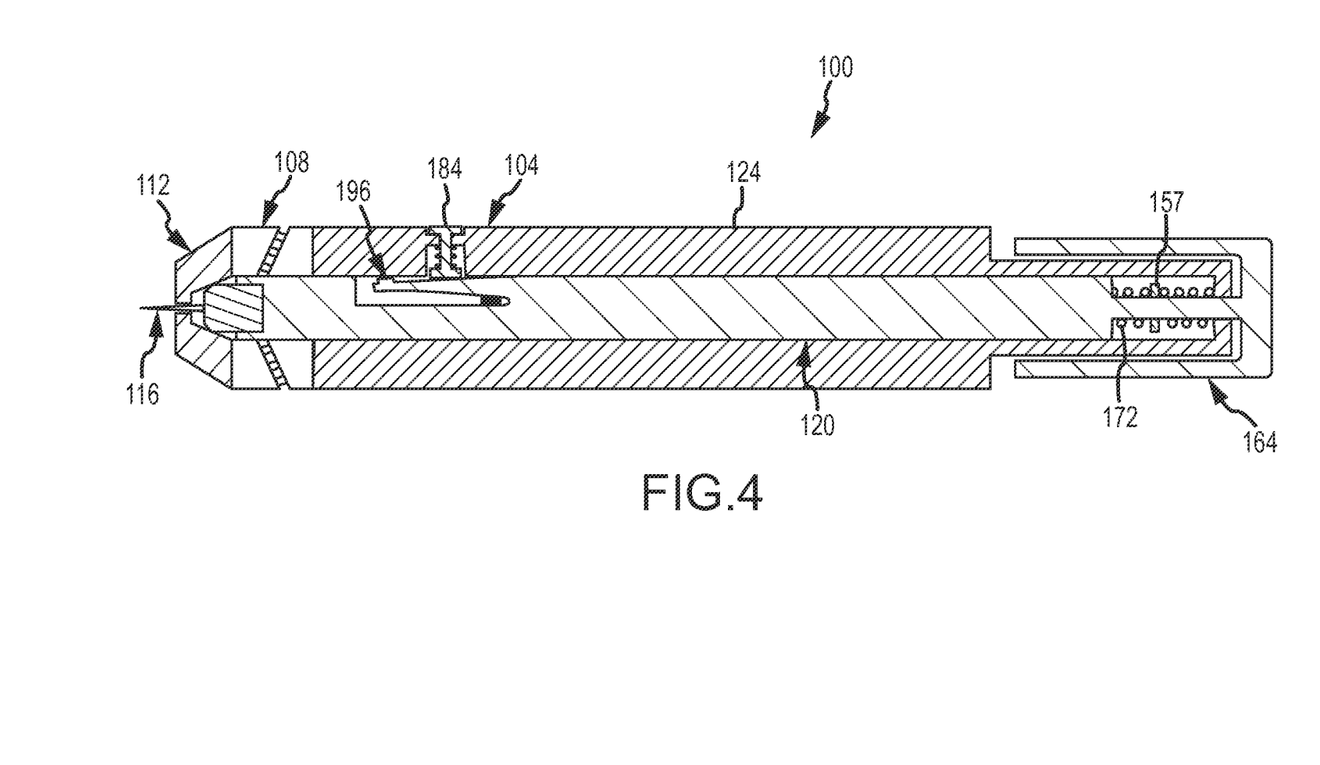
FIG. 4 is a cross-sectional view similar to that in FIG. 3, but with the piston and lancet being in a lancing position.
Figure 5:
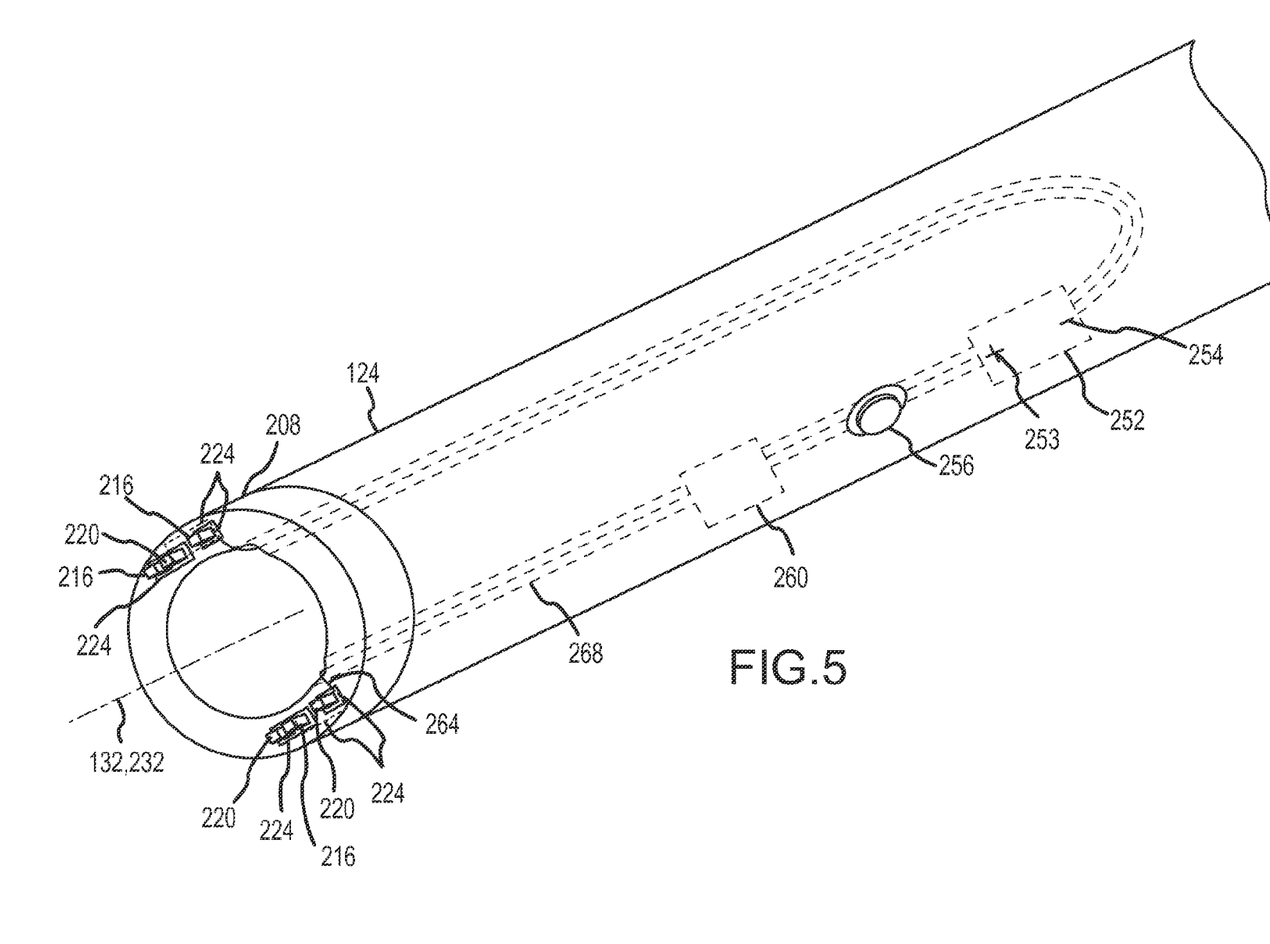
FIG. 5 is another perspective view of the lancing device with some components removed for clarity.

Turning now to FIG. 3, the triggering button 184 is situated in the cavity 192 above the protrusion 196, and is normally urged towards the central axis 132 of the lumen 128 (e.g., perpendicularly) by a trigger spring 204 (i.e., in the absence of the protrusion 196 contacting the triggering button 184). However, when the protrusion 196 enters the cavity 192 as discussed above, the protrusion 196 urges the triggering button 184 away from the central axis 132 so that it protrudes past the outer surface 130 of the housing wall 124. Thereafter, when the triggering button 184 is pushed inwardly or towards the central axis 132 (e.g., via a user depressing the triggering button 184), the protrusion 196 becomes dislodged from the wall 200 of the cavity 192. As a result, the actuating spring 172 drives the piston 120 and/or flange 157 forward and therefore the lancet 116 forward towards the body tissue for lancing as illustrated in FIG. 4.

At the point when the lancet tip 148 has punctured the body tissue, the actuating spring 172 has extended beyond its relaxed state (shown in FIG. 2). Thus, just after the lancet tip 148 has punctured the body tissue, the actuating spring 172 will tend to move back towards the relaxed state shown in FIG. 2. In this regard, the actuating spring 172 will correspondingly pull on the flange 157 which will pull the piston 120 and the lancet 116 back to the position shown in FIG. 2 such that the lancet tip 148 is limited from inadvertently puncturing body tissue or another surface. As an alternative or in addition to the flange 157, a "return" spring (not shown) may be provided between a) the second end 136 of the piston 120 and/or the lancet block 144, and b) some portion of the cooling ring 112, Peltier device 108 and/or housing 104. In this regard, movement of the piston 120 into the lancing position shown in FIG. 4 would compress the return spring and store potential energy in the return spring. Thereafter and upon return to a relaxed state of the return spring, the return spring would urge the piston 120 and the lancet 116 away from the body tissue and back into the relaxed position shown in FIG. 2 (or at least to some withdrawn position within the lancing device 100). It will be appreciated that the various springs discussed herein can be selected (e.g., based on type, number of turns, spring constant, diameter) to provide the functionalities discussed herein.

With reference now to FIGS. 1-5, the Peltier device 108 serves to, upon a current being sent through the Peltier device 108 as is well known in the art, create a "hot" surface or side 208 and a "cold" surface or side 212 for reducing the localized sensation of pain on a body tissue associated with a lancing procedure as will be described below. That is, the temperature of the hot side 208 is adapted to increase and the temperature of the cold side 212 is adapted to decrease upon a current being received through the Peltier device 108. Each of the hot and cold sides 208, 212 may be any appropriate electrically insulative but thermally conductive material (e.g., ceramic plates or substrates). As shown, the hot and cold sides 208, 212 may generally be in the cross-sectional shape of the housing wall 124, and may be separated by a series of first and second blocks or portions of dissimilar metals 216, 220 (e.g., P-type and N-type Bismuth Telluride dice, most clearly shown in FIG. 5).

As is known in the art, the first and second metals may be electrically connected in series and thermally connected in parallel between the hot and cold sides 208, 212, and a series of electrically conductive members 224 (e.g., copper pads or traces) may be appropriately attached to the hot and cold sides 208, 212 and to the first and second metals 216, 220 to maintain the various electrical connections inside the Peltier device 108. For instance, solder may be used at the various connection joints to enhance the electrical connections and hold the Peltier device 108 together. More or fewer of the first and second metals 216, 220 and electrically conductive members 224 may be shown than in FIG. 5 in any appropriate arrangement as will be appreciated by those in the art. While the intersection between the hot and cold sides 208, 212 has been shown in FIGS. 2-4 as converging towards the central aperture 244 (i.e., the intersection is disposed other than perpendicular to the central axes 132, 232, 248), it is also contemplated that this intersection could be at least substantially perpendicular to the central axes 132, 232, 248.

As shown, the hot side 208 of the Peltier device 108 is in thermal contact with the second end 126 of housing wall 124 so that thermal energy generated and received by the hot side 208 when a current is passed through the Peltier device 108 may be passed directly to the housing wall 124. Thus, the housing wall 124 may function as a heat accumulator by accumulating thermal energy from the hot side 208 and spreading out such thermal energy along a length of the housing wall 124. As the housing wall 124 draws more and more thermal energy from the hot side 208, the hot side 208 may be able to accept additional thermal energy which may allow the cold side 212 give up more and more thermal energy and correspondingly further reduce in temperature.

The hot side 208 may be thermally interconnected to the housing wall 124 in any appropriate manner such as by welding, adhesives, and the like. In one arrangement, the hot side 208 (and thus the entire Peltier device 108) may be thermally interconnected to the housing wall 124 via a threaded connection (not shown). In this regard, the Peltier device 108 may be conveniently removed when it is desired to, for instance, replace the lancet 116 with a new, sterile lancet 116, and then reattached so as to again be in thermal connection with the housing wall 124. It can also be seen that the Peltier device 108 includes a central aperture 228 having a central axis 232 extending through the Peltier device 108 between the hot and cold sides 208, 212, and the central axis 232 of the Peltier device 108 is at least substantially collinear with the central axis 132 of the housing wall 124. This arrangement provides a number of advantages such as providing for a more compact lancing device 100 (as opposed to a lancing device having a cooling unit on another portion of the lancing device 100), allowing for a more direct transfer of thermal energy from the Peltier device 108 to the housing wall 124, and being in a position that surrounds the lancet 108 and hence the body tissue around the puncture point in the body tissue.

With continued reference to FIGS. 1-4, the lancing device also may include a thermally conductive cooling ring 112 of any appropriate shape and dimensions that is thermally interconnected to the cold side 212 of the Peltier device 108 and that is operable to make contact with the patient's body tissue around the puncture point in the body tissue. For instance, the cooling ring 112 may be generally frustoconically shaped having first and second opposing surfaces 236, 240 and a central aperture 244 having a central axis 248 therethrough between the first and second opposing surfaces 236, 240 for receipt of the lancet tip 148. As seen, at least substantially an entire portion of the first surface 236 is thermally connected to the cold side 212 of the Peltier device 108. This allows for greater transfer of thermal energy from the cooling ring 112 (received from the body tissue) to the cold side 212 and eventually to the hot side 208 and the housing wall 124. The cooling ring 112 may be constructed of and appropriate thermally conductive material (e.g., aluminum).

Similar to the interconnection of the hot side 208 with the housing wall 124, the cooling ring 112 may be thermally interconnected to the cold side in any appropriate manner such as by welding, adhesives, a threaded connection, and the like. It can also be seen that the central axis 248 of the cooling ring 112 is at least substantially collinear with both the central axis 232 of the Peltier device 108 and the central axis 132 of the housing wall 124. As discussed previously, this arrangement provides for a more compact lancing device 100, allows for a more direct transfer of thermal energy from the cooling ring 112 to the cold side 212, and allows the cooling ring 112 to surround the lancet 116 and hence the body tissue around the puncture point in the body tissue. As can also be seen, the central aperture 244 of the cooling ring generally reduces in diameter in a direction from the first surface 236 towards the second surface 240 of the cooling ring 112. Stated otherwise, at least a portion of the diameter of the central aperture of the cooling ring 112 is less than that of the Peltier device 108. In this regard and as will be appreciated, the second surface 240 of the cooling ring 112 may be designed so as to contact the body tissue substantially adjacent to the puncture point in the body tissue. Locating the second surface 240 of the cooling ring in such relation to the puncture point in the body tissue may further chill the body tissue near or adjacent the puncture point to further reduce localized pain associated with the lancing procedure.

To power the Peltier device 108 to allow the cooling ring 112 to chill the body tissue around the puncture point, any appropriate circuitry, wiring and componentry may be used as would be known to those in the art. For instance and with reference now to FIG. 5 (note that some components of the lancing device 100 have been removed for clarity), a DC power source in the form of a battery 252 (e.g., a 3 V battery, 2 1.5 V batteries, shown schematically) with positive and negative terminals 253, 254 may be provided and appropriately located in a portion of the housing wall 124 (or other appropriate location). In one arrangement, a battery compartment may be appropriately located that can be accessed by a removable or slidable door or cover (not shown). Additionally, a switch 256 in any appropriate form (e.g., push button, rocker switch, toggle switch) may be provided so as to protrude from the outside surface 130 of the housing wall 124 (or any sheath or shell surrounding the housing wall 124) to selectively allow power from the battery 252 to reach the Peltier device 108. A microcontroller 260 (shown schematically) may also be provided with any appropriate componentry (e.g., microprocessor, memory, I/O ports, DC/DC converter, temperature sensor) to, for instance, control the timing and power delivered to the Peltier device 108. The Peltier device 108, battery 252, switch 256 and microcontroller 260 may be appropriately electrically interconnected by wiring 264, and the wiring may be appropriately contained and wound through passageways 268 within the housing wall 124 (or other appropriate location(s)).

In operation, the sleeve cap 164 may be withdrawn or otherwise pulled back until the protrusion 196 enters and "locks" into the cavity 192. Thereafter, the Peltier device 108 may be activated by switch 256 so as to cool the cooling ring 112 to a temperature selected to desensitize the skin. In one arrangement, a dial or other device can be provided to allow a user to selectively adjust the temperature of the cooling ring 112. The microcontroller 260 may contain logic operable to control the power and timing in relation to current passed to the Peltier device 108. In any event, the lancing device 100 may then be positioned such that the second surface 240 of the cooling ring 112 contacts a portion of body tissue (e.g., skin) and so that the central aperture 244 is at least substantially aligned over the particular portion of body tissue that is desired to be punctured. After a period of time has elapsed that allows the body tissue to become desensitized (e.g., 3-5 seconds), the triggering button 184 may be depressed which fires the lancet tip 148 into the body tissue. In one arrangement, a temperature sensor can be associated with or embedded within the lancing device to measure the temperature in the body tissue near the cooling ring 112. Upon the temperature decreasing to a level corresponding to reduced pain sensitivity, the microcontroller 260 can issue a signal (e.g., audible, visual) indicating that the triggering button 184 can be depressed. After the puncturing has occurred, the lancet tip withdraws back into at least a portion of the cooling ring 112, Peltier device 108 and/or housing wall 124 as discussed above to limit the lancet tip 148 from inadvertently puncturing another body tissue or surface. At this point, the lancing device 100 may be prepared for reuse (sterilizing and/or replacing the cooling ring 112, Peltier device 108, lancet 116, etc.).

The apparatuses disclosed herein can be constructed of any appropriate materials and combinations of such materials via any appropriate manufacturing methods such as casting, forming, machining, welding, extruding and/or the like. As discussed earlier, aligning the central axes 132, 232, 248 of the housing wall 124, Peltier device 108 and cooling ring 112 (and/or constructing the housing wall 124, Peltier device 108, and/or cooling ring 112 to have substantially similar outer diameters) allows for a more compact "pen-like" device, allows for increased thermal energy transfer between the above described components, and concentrates the cooling and desensitization effects of the Peltier device 108 and cooling ring 112 directly around the puncture point on the body tissue. Additionally, the substantially full, flush contact between a) the housing wall 124 and the hot side 208 of the Peltier device 108, and b) the cooling ring 112 and the cold side 212 of the Peliter device 108 further provides for such increased thermal energy transfer (and/or correspondingly more efficient Peltier device 108). Moreover, providing the housing wall 124 in the form of an elongated heat accumulator advantageously allows heat received from the hot side 208 of the Peltier device 108 to be spread out and distributed along the length of the housing wall without, for instance, the need for heat sinks, fans, etc. For instance, it has been found that a housing wall that is between about 70-130 mm long, or in another arrangement between about 90-110 mm long provides for adequate accumulation of thermal energy in the housing wall 124 so that the temperature of the cooling ring 112 can be reduced to a desired magnitude.

Any of the embodiments, arrangements, or the like discussed herein may be used (either alone or in combination with other embodiments, arrangement, or the like) with any of the disclosed aspects. Merely introducing a feature in accordance with commonly accepted antecedent basis practice does not limit the corresponding feature to the singular (e.g., indicating that the device includes "the Peltier device" alone does not mean that the device includes only a single Peltier device). Moreover, any failure to use phrases such as "at least one" also does not limit the corresponding feature to the singular (e.g., indicating that the lancing device includes "a Peltier device" alone does not mean that the lancing device includes only a single Peltier device). Use of the phrase "at least generally," "at least partially," "substantially" or similar phraseology in relation to a particular feature encompasses the corresponding characteristic and insubstantial variations thereof. For example, central axes of the housing wall, Peltier device and cooling ring being "substantially collinear" or "at least substantially collinear" covers both an insubstantial variation of the central axes being collinear in addition to the central axes being collinear. Finally, a reference of a feature in conjunction with the phrase "in one embodiment" does not limit the use of the feature to a single embodiment.

While the disclosure has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences).

Accordingly, it should be understood that only the preferred embodiment and variants thereof have been shown and described and that all changes and modifications that come within the spirit of the disclosure are desired to be protected.

What is claimed:

1. A lancing device, comprising:
   an outer housing comprising an outer housing wall having a first end, a second end defining a lancing opening, and a chamber extending between the first and second ends that includes a central axis, wherein the outer housing wall comprises a material that allows the outer housing wall to accumulate heat;
   a Peltier device for absorbing heat from a patient's skin and passing heat to the outer housing wall, the Peltier device comprising:
     a hot side having a hot surface in thermal contact with the outer housing wall;
     a cold side having a cold surface interconnected to the hot side, the cold side adapted to receive heat from the patient's skin and pass the heat to the hot side; and
     a central aperture extending through the Peltier device between the hot and cold surfaces, wherein the central aperture includes a central axis, and wherein the central axes of the chamber and the central aperture are substantially collinear;
   a lancet translationally mounted within the chamber for movement between at least a cocked position and a lancing position, the lancet having a lancet tip configured for contact with the patient's skin in the lancing position;
   a cooling ring for cooling the patient's skin, the cooling ring including a first surface in thermal contact with the cold surface, an opposed second surface configured for contact with the patient's skin, and a central aperture extending through the cooling ring between the first and second surfaces for receipt of the lancet tip in the lancing position, wherein the central aperture of the cooling ring includes a central axis, and wherein the central axis of the chamber, the central axis of the Peltier device and the central axis of the cooling ring are substantially collinear; and
   a power source mounted within the outer housing that is electrically interconnected to the Peltier device, wherein a temperature of the cold side is adapted to decrease and a temperature of the hot side is adapted to increase when the power source passes a current through the Peltier device.

2. The lancing device as recited in claim 1, wherein the outer housing wall includes a length extending between the first and second ends, and the Peltier device includes a length extending between the hot and cold sides, wherein the length of the outer housing wall is greater than the length of the Peltier device.

3. The lancing device as recited in claim 2, wherein the length of the outer housing wall is between about 70-130 mm.

4. The lancing device as recited in claim 3, wherein the length of the outer housing wall is between about 90-110 mm.

5. The lancing device as recited in claim 1, wherein at least substantially an entirety of the cold surface is in thermal contact with the first surface of the cooling ring.

6. The lancing device as recited in claim 1, wherein a diameter of the central aperture of the cooling ring is less than a diameter of the central aperture of the Peltier device.

7. The lancing device as recited in claim 1, wherein an outer diameter of the outer housing wall is at least substantially equal to an outer diameter of the Peltier device.

8. The lancing device as recited in claim 1, wherein the power source includes a battery.

9. The lancing device as recited in claim 1, wherein the outer housing wall includes one or more metals.

10. The lancing device as recited in claim 1, wherein the outer housing wall includes at least one of copper, aluminum, and combinations thereof.

11. The lancing device as recited in claim 1, wherein the cooling ring includes aluminum.

12. An apparatus, comprising:
    an elongated cylindrical heat accumulator, the heat accumulator including a first end, a second end defining a lancing opening, a chamber extending between the first and second ends, a length extending between the first and second ends, and a longitudinal axis extending along the chamber through a center of the heat accumulator;
    a Peltier device thermally connected to the second end of the heat accumulator, the Peltier device including a hot side having a hot surface, a cold side having a cold surface, a length extending between the hot and cold surfaces, and a central aperture extending through the Peltier device between the hot and cold surfaces, wherein a central axis of the central aperture of the Peltier device and the longitudinal axis of the chamber are substantially collinear;
    a cooling ring thermally connected to the Peltier device and opposed from the heat accumulator, the cooling ring including a central aperture extending through the cooling ring, wherein a central axis of the central aperture of the cooling ring is collinear with the central axis of the central aperture of the Peltier device and the longitudinal axis of the chamber, wherein the cooling ring includes a first surface in thermal contact with the cold surface and an opposed second surface configured for contact with a patient's skin, and wherein at least substantially an entirety of the cold surface is in thermal contact with the first surface of the cooling ring; and
    a lancet translationally mounted within the heat accumulator for movement between at least a cocked position and a lancing position, the lancet having a lancet tip configured for contact with the patient's skin when the lancet is in the lancing position.

13. The apparatus as recited in claim 12, further including a battery mounted within the heat accumulator that is electrically interconnected to the Peltier device, wherein the Peltier device is adapted to receive heat collected from the patient's skin from the cooling ring and pass the received heat to the heat accumulator to cool the patient's skin when the battery passes a current through the Peltier device as part of a lancing procedure on the patient's skin.

14. The apparatus as recited in claim 12, wherein a diameter of the central aperture of the cooling ring is less than a diameter of the central aperture of the Peltier device.

* * * * *